(12) United States Patent
Xu

(10) Patent No.: US 9,993,511 B2
(45) Date of Patent: *Jun. 12, 2018

(54) PHARMACEUTICAL COMPOSITIONS FOR TREATING THERMAL INJURIES AND WOUNDS COMBINED WITH BONE INJURIES

(71) Applicant: Kevin Peng Xu, Arcadia, CA (US)

(72) Inventor: Rongxiang Xu, Beijing (CN)

(*) Notice: Subject to any disclaimer, the term of this patent is extended or adjusted under 35 U.S.C. 154(b) by 16 days.

This patent is subject to a terminal disclaimer.

(21) Appl. No.: 15/362,674

(22) Filed: Nov. 28, 2016

(65) Prior Publication Data

US 2017/0072000 A1    Mar. 16, 2017

Related U.S. Application Data

(63) Continuation of application No. 14/763,126, filed as application No. PCT/CN2013/076412 on May 29, 2013, now Pat. No. 9,533,020.

(30) Foreign Application Priority Data

Jan. 24, 2013  (CN) .......................... 2013 1 0027487

(51) Int. Cl.
| | | |
|---|---|---|
| *A61K 36/00* | (2006.01) | |
| *A61K 36/756* | (2006.01) | |
| *A61K 35/62* | (2006.01) | |
| *A61K 35/644* | (2015.01) | |
| *A61K 36/14* | (2006.01) | |
| *A61K 36/539* | (2006.01) | |
| *A61K 36/66* | (2006.01) | |
| *A61K 36/718* | (2006.01) | |
| *A61K 36/53* | (2006.01) | |
| *A61K 36/185* | (2006.01) | |

(52) U.S. Cl.
CPC ............ *A61K 36/756* (2013.01); *A61K 35/62* (2013.01); *A61K 35/644* (2013.01); *A61K 36/14* (2013.01); *A61K 36/185* (2013.01); *A61K 36/53* (2013.01); *A61K 36/539* (2013.01); *A61K 36/66* (2013.01); *A61K 36/718* (2013.01)

(58) Field of Classification Search
CPC ..................................................... A61K 36/00
USPC ....................................................... 424/725
See application file for complete search history.

(56) References Cited

FOREIGN PATENT DOCUMENTS

CN    1048160 A  *  1/1991

* cited by examiner

*Primary Examiner* — Michael V Meller
(74) *Attorney, Agent, or Firm* — Ice Miller LLP

(57) ABSTRACT

The present invention relates to a pharmaceutical composition for treating thermal injuries and wounds combined with bone injuries. More specifically, the present invention relates to a pharmaceutical composition for treating thermal injuries and wounds combined with bone injuries characterized in consisting of 4%-12% beeswax and 88%-96% sesame oil extract containing such raw materials as *Radix Scutellariae, Coptis Chinensis, Cortex Phellodendri, Pericarpium Papaveris* and *Lumbricus* by weight based on the total weight of the said composition, wherein the content of *Radix Scutellariae, Coptis Chinensis, Cortex Phellodendri, Pericarpium Papaveris* or *Lumbricus* based on their dry weight is respectively 1%-6% of the total weight of the sesame oil. The pharmaceutical composition of the present invention can treat thermal injuries involving human skin, subcutaneous tissues and bones, as well as involving bone wounds, especially open fractures, deep thermal injuries combined with bone injuries, and deep thermal injuries combined with bone necrosis caused by trauma, such as deep burns combined with bone injuries or bone necrosis.

20 Claims, 16 Drawing Sheets

PHARMACEUTICAL COMPOSITIONS FOR TREATING THERMAL INJURIES AND WOUNDS COMBINED WITH BONE INJURIES

CROSS-REFERENCE TO RELATED APPLICATIONS

The present application is a continuation of U.S. patent application Ser. No. 14/763,126, which is a U.S. nationalization of PCT Application No. PCT/CN2013/076412, filed May 29, 2013, which claims the priority benefit of Chinese Patent Application Serial No. CN201310027487.8, filed Jan. 24, 2013, the text and drawings of all of which are hereby incorporated by reference in their entireties.

FIELD OF THE INVENTION

The present invention relates to a pharmaceutical composition, specifically, to a botanical pharmaceutical composition for the treatment of thermal injury and wounds complicated by bone injury.

BACKGROUND OF THE INVENTION

The inventor of the present invention disclosed a pharmaceutical composition for the treatment of thermal injury of warm-blooded animals or human beings in his Chinese Patent Application No. 93100276.1, characterized in that said composition by consisting of 3%-15% of beeswax and 85%-97% of sesame oil extract containing such raw materials as *Radix Scutellariae, Coptis Chinensis, Cortex Phellodendri, Pericarpium Papaveris* and *Lumbricus* by weight based on the total weight of the said composition, of which the content of *Radix Scutellariae, Coptis Chinensis, Cortex Phellodendri, Pericarpium Papaveris* or *Lumbricus* based on their dry weight is respectively 2%-10% of the total weight of the sesame oil.

The said thermal injury (thermal damage) refers to the degeneration and necrosis injuries of cells and tissues of mammal including human caused by temperature changes, such as scalds, burns, low-temperature skin damage, cold injury, electrical injury, chemical solution or radiation induced injuries and the like. The affected human tissues vary with the severities of thermal injuries or wounds and ulcers, with epidermis, dermis, subcutaneous tissue, muscle, and bone involved successively.

Bone injury of human includes shin bone injury and cartilage injury.

It is well known for the person skilled in the art that thermal injury or wounds of different causes may commonly be complicated by bone injury in clinical practices, such as deep burn injury often involves the degeneration and necrosis of bone. In the prior art, especially Chinese Patent Application No. 93100276.1 disclosed a pharmaceutical composition for the treatment of thermal injury of warm-blooded mammal or human beings, wherein the said composition can only be used for treating traumatic wounds deep to periosteum. However, after the painstaking research, the present inventor develops a new optimized formula based on the formula above which is both effective for the treatment of thermal injury of human skin, subcutaneous tissues and bones as well as wounds and ulcers involving bones, especially effective for the treatment of open injury caused by traumas, deep thermal injury complicated by bone injury and deep thermal injury complicated by osteonecrosis, such as deep burns complicated with bone injury or osteonecrosis. The pharmaceutical composition according to the present invention is an improvement of Chinese Patent Application No. 93100276.1.

SUMMARY OF THE INVENTION

The object of the present invention is thus to provide a botanical pharmaceutical composition for the treatment of thermal injury and wounds complicated with bone injury.

Thus, the first aspect of the present invention involves a pharmaceutical composition for the treatment of thermal injury and wounds complicated with bone injury, characterized in that said pharmaceutical composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of said composition, of which the content of *Radix Scutellariae, Coptis Chinensis, Cortex Phellodendri, Pericarpium Papaveris* or *Lumbricus* based on their dry weight is respectively 1%-6% of the total weight of the sesame oil.

Preferably, the content of *Radix Scutellariae, Coptis Chinensis, Cortex Phellodendri, Pericarpium Papaveris*, or *Lumbricus* based on their dry weight is respectively 2%-4% of the total weight of the sesame oil.

More preferably, the content of *Radix Scutellariae, Coptis Chinensis, Cortex Phellodendri, Pericarpium Papaveris* or *Lumbricus* based on their dry weight is respectively 3% of the total weight of the sesame oil.

Most preferably, the said composition consists of:

1) 4% of beeswax and 96% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* or *Lumbricus* based on their dry weight is respectively 6% of the total weight of the sesame oil;

2) 6% of beeswax and 94% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* or *Lumbricus* based on their dry weight is respectively 3% of the total weight of the sesame oil;

3) 8% of beeswax and 92% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* or *Lumbricus* based on their dry weight is respectively 1% of the total weight of the sesame oil;

4) 8% of beeswax and 92% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* and *Lumbricus* based on their dry weight is respectively 5.5%, 5.5%, 5.5%, 2.2% and 2.2% of the total weight of the sesame oil;

5) 10% of beeswax and 90% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* and *Lumbricus* based on their dry weight is respectively 2% of the total weight of the sesame oil;

6) 12% of beeswax and 88% of sesame oil extract containing such raw materials as *Radix Scutellariae, Coptis Chinensis, Cortex Phellodendri, Pericarpium Papaveris* and *Lumbricus* by weight based on the total weight of said composition, wherein the content of *Radix Scutellariae, Coptis Chinensis, Cortex Phellodendri, Pericarpium Papaveris* and *Lumbricus* based on their dry weight is respectively 1% of the total weight of the sesame oil;

Preferably, the said bone injury refers to open traumatic injury complicated by fracture, deep thermal injury with bone injury or osteonecrosis.

More preferably, the said bone injury refers to bone injury combined with periosteum damage.

In the second aspect of the present invention, it involves the use of the pharmaceutical composition in the preparation of medicaments for the treatment of thermal injury complicated by bone injury, wherein said composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the content of *Radix Scutellariae, Coptis Chinensis, Cortex Phellodendri, Pericarpium Papaveris* or *Lumbricus* based on their dry weight is respectively 1%-6% of the total weight of the sesame oil.

Preferably, the content of *Radix Scutellariae, Coptis Chinensis, Cortex Phellodendri, Pericarpium Papaveris,* or *Lumbricus* based on their dry weight is respectively 2%-4% of the total weight of the sesame oil.

More preferably, the content of *Radix Scutellariae, Coptis Chinensis, Cortex Phellodendri, Pericarpium Papaveris,* or *Lumbricus* based on their dry weight is respectively 3% of the total weight of the sesame oil.

Preferably, the said bone injury refers to open traumatic injury complicated by fracture, deep thermal injury with bone injury or osteonecrosis.

More preferably, the said bone injury refers to bone injury combined with periosteum damage.

In the third aspect of the present invention, it involves a pharmaceutical composition consisting of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the content of *Radix Scutellariae, Coptis Chinensis, Cortex Phellodendri, Pericarpium Papaveris* and *Lumbricus* based on their dry weights is 1%-6% of the total weight of the sesame oil, and said composition is used for the treatment of thermal injury complicated by bone injury.

Preferably, the said thermal injury refers to open traumatic injury complicated by fracture, deep thermal injury with bone injury or osteonecrosis.

In the fourth aspect of the present invention, it involves a method of treating open traumatic injury complicated by fracture, deep thermal injury with bone injury and osteonecrosis, comprising administration of effective dose of pharmaceutical composition to the patient, wherein said composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the content of *Radix Scutellariae, Coptis Chinensis, Cortex Phellodendri, Pericarpium Papaveris* or *Lumbricus* based on their dry weight is respectively 1%-6% of the total weight of the sesame oil.

In other words, based on the prior art, the present inventor made appropriate adjustment to the proportions of the raw materials, which produced unexpected technical effect on the treatment of thermal injury complicated by bone injury and simple bone injury such as open fracture. Especially, the inventor found that when the contents of *Radix Scutellariae, Coptis Chinensis, Cortex Phellodendri, Pericarpium Papaveris* and *Lumbricus* are beyond the range of 1%-6% by dry weight based on the total weight of the sesame oil respectively, there are no therapeutic effects on bone injury, while when their contents are within the range of 1%-6% respectively, the composition can bring significant therapeutic effects on bone injury. More especially, when the contents of these raw materials are 2%-4%, particularly 3%, by dry weight based on the total weight of the sesame oil respectively, the therapeutic effects of the composition are much better.

The said bone injury in the present invention includes open traumatic injury complicated by bone fracture, deep thermal injury with bone injury and osteonecrosis. Particularly the said bone injury refers to bone injury with periosteum damage. For instance, for the open traumatic injury complicated by bone injury, such as the open bone fracture commonly seen in a catastrophe (e.g. earthquake), if not treated timely, it may often result in amputation and lifelong disability of victims as it is susceptible to infection due to serious wound contamination. Therefore, the present invention is to provide a pharmaceutical composition that can be applied in treating open bone fracture directly, and thus also provide a pharmaceutical composition of treating bone injury, characterized in that said composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the contents of these raw materials based on their dry weights are 1%-6% of the total weight of the sesame oil respectively.

The present invention also provides a method of treating open traumatic injury complicated by bone fracture, deep thermal injury with bone injury and osteonecrosis, comprising administration of an effective dose of the pharmaceutical composition onto the affected locations, wherein the said pharmaceutical composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the contents of these raw materials based on their dry weights are 1%-6% of the total weight of the sesame oil respectively. Preferably, the contents of these raw materials based on their dry weights are 2%-4% of the total weight of the sesame oil respectively.

In addition, the invention also provides the use of a pharmaceutical composition in the preparation of medicaments for the treatment of bone injury, wherein the said composition consists of 4%-12% of beeswax and 88%-96% of sesame oil extract containing such raw materials as *Radix Scutellariae, Coptis Chinensis, Cortex Phellodendri, Pericarpium Papaveris* and *Lumbricus* by weight based on the total weight of the said composition, of which the contents of these raw materials based on their dry weights are 1%-6% of the total weight of the sesame oil respectively.

A method of treating open traumas complicated by fracture and/or deep thermal injury with bone injury and/or osteonecrosis is disclosed, comprising administration of an effective dose of a pharmaceutical composition onto the affected locations, wherein said pharmaceutical composition comprises 4%-12% of beeswax by weight based on the total weight of said composition, and 88%-96% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein each of the one or more components based on their dry weight is 1%-6% of the total weight of the sesame oil. In some embodiments, each of the one or more components based on their dry weight is 2%-4% of the total weight of the sesame oil. In some embodiments, each of the one or more components based on their dry weight is 3% of the total weight of the sesame oil.

In some embodiments, the pharmaceutical composition comprises 4% of beeswax by weight based on the total weight of said composition, and 96% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein the content of each of the one or more components based on their dry weight is 6% of the total weight of the sesame oil.

In some embodiments, the pharmaceutical composition comprises 6% of beeswax by weight based on the total weight of said composition, and 94% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein the content of each of the one or more components based on their dry weight is 3% of the total weight of the sesame oil.

In some embodiments, the pharmaceutical composition comprises 8% of beeswax by weight based on the total weight of said composition, and 92% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein the content of each of the one or more components based on their dry weight is 1% of the total weight of the sesame oil.

In some embodiments, the pharmaceutical composition comprises 8% of beeswax by weight based on the total weight of said composition, and 92% of sesame oil extract by weight based on the total weight of said composition, wherein the sesame oil extract contains 5.5% *Radix Scutellariae*, 5.5% *Coptis Chinensis*, 5.5% *Cortex Phellodendri*, 2.2% *Pericarpium Papaveris*, and 2.2% Lumbricus, each component by weight based on the total weight of the sesame oil.

In some embodiments, the pharmaceutical composition comprises 10% of beeswax by weight based on the total weight of said composition, and 90% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein the content of each of the one or more components based on their dry weight is 2% of the total weight of the sesame oil.

In some embodiments, the pharmaceutical composition comprises 12% of beeswax by weight based on the total weight of said composition, and 88% of sesame oil extract by weight based on the total weight of said composition, wherein the sesame oil extract contains one or more components selected from the group consisting of *Radix Scutellariae, Coptis Chinensis, Cortex Phellodendri, Pericarpium Papaveris*, and *Lumbricus*, and any combination thereof, wherein the content of each of the one or more components based on their dry weight is 1% of the total weight of the sesame oil.

In some embodiments, said bone injury comprises bone injury with periosteum damage.

In some embodiments, said administration comprises applying the pharmaceutical composition onto the affected locations with a thickness of about 1-3 mm. In some embodiments, said administration comprises applying the pharmaceutical composition onto the affected locations with a thickness of 3 mm.

In some embodiments, the pharmaceutical composition is administered as a multiple dose treatment. In some embodiments, the multiple dose treatment occurs over a time period of from 7 to 40 days. In some embodiments, the multiple dose treatment occurs over a time period of 7 days. In some embodiments, the multiple dose treatment occurs over a time period of 10 days. In some embodiments, the multiple dose treatment occurs over a time period of 40 days.

In some embodiments, the open traumas complicated by fracture and/or deep thermal injury with bone injury and/or osteonecrosis are on a warm-blooded animal. In some embodiments, the open traumas complicated by fracture and/or deep thermal injury with bone injury and/or osteonecrosis are on a human being. In some embodiments, the bone injury is selected from shin bone injury, skull bone injury, and/or cartilage injury.

According to the specific experiments, only the low doses of *Radix Scutellariae, Coptis Chinensis, Cortex Phellodendri, Pericarpium Papaveris*, and *Lumbricus* in the sesame oil extract (1-6% of the total weight of the sesame oil respectively based on their dry weights) has the therapeutic effect on thermal injuries, wounds, and ulcers combined with bone injury. In contrast, when the contents of *Radix Scutellariae, Coptis Chinensis, Cortex Phellodendri, Pericarpium Papaveris*, and *Lumbricus* in the sesame oil extract are higher than 6% or lower than 1%, there is no therapeutic effect on thermal injuries and wounds combined with bone injuries. According to the analysis of the inventor, the higher concentration of *Radix Scutellariae, Coptis Chinensis, Cortex Phellodendri, Pericarpium Papaveris*, and *Lumbricus* may inhibit the cell growth of thermal injury and the wounds combined with bone injuries, thus it has no therapeutic effect on thermal injuries and wounds combined with bone injuries. And the lower concentration of *Radix Scutellariae, Coptis Chinensis, Cortex Phellodendri, Pericarpium Papaveris*, and *Lumbricus* in the sesame oil extract does not reach the therapeutic dosage concentration, which will cause the treatment failure.

Regarding to the proportion of *Radix Scutellariae, Coptis Chinensis, Cortex Phellodendri, Pericarpium Papaveris*, and *Lumbricus* in the sesame oil extract, it has found that the specific proportion of them has no relevant impact on the treatment result, as long as they occupy 1-6% of the total weight of the sesame oil extract respectively based on their dry weights.

DETAILED DESCRIPTION OF THE INVENTION

Figure 1:
FIG. 1 is the photo of the deep burn (chemical) injury of shank and foot combined with bone injury in experimental example 1.

The present invention will be described in detail according to the unlimited examples below. It should be understood by the person skilled in the art that many modifications can be made for the present invention without departing from the spirit of the present invention, such modifications also fall into the scope of the present invention.

Unless indicated otherwise, the experimental methods in the following are all conventional methods and all the experimental materials are available commercially.

Example 1

According to the method disclosed in example 1 of Chinese Patent Application No. 93100276.1, the raw materials of *Radix Scutellariae, Coptis Chinensis, Cortex Phellodendri, Lumbricus* and *Pericarpium Papaveris* were weighed each 6 kg and crushed according to the common method in the art.

100 Kg of sesame oil bought in market was added into the extraction kettle as extract agent and heated to 120° C. Then the raw materials above were added into the kettle with hot sesame oil and stirred at 150° C. for 45 min.

The extractant was subjected to filtration, removing of the filter residues and precipitation at room temperature. The supernatant was collected to obtain 100 Kg of extractant which is the sesame oil containing the above raw materials.

96 Kg of the resulted sesame oil containing raw materials above was mixed with 4 Kg of beeswax from the market according to the common method in the art to afford 100 Kg of pharmaceutical composition 1.

Example 2

The pharmaceutical composition was prepared according to the method of example 1 except that the composition was consist of 6 Kg of beeswax and 94 Kg of sesame oil extract containing 3 kg of *Radix Scutellariae, Coptis Chinensis, Cortex Phellodendri, Pericarpium Papaveris* and *Lumbricus* respectively, and the temperature of sesame oil was kept at 160° C. and stirred for 40 min to afford pharmaceutical composition 2.

Example 3

The pharmaceutical composition was prepared according to the method of example 1 except that the composition was consist of 8 Kg of beeswax and 92 Kg of sesame oil extract containing 1 kg of *Radix Scutellariae, Coptis Chinensis, Cortex Phellodendri, Pericarpium Papaveris* and *Lumbricus* respectively, and the temperature of sesame oil was kept at 155° C. and stirred for 40 min to afford pharmaceutical composition 3.

Example 4

The pharmaceutical composition was prepared according to the method of example 1 except that the composition was consist of 8 Kg of beeswax and 92 Kg of sesame oil extract containing 5.5 kg of *Radix Scutellariae*, 5.5 kg of *Coptis Chinensis*, 5.5 kg of *Cortex Phellodendri*, 2.2 kg of *Pericarpium Papaveris* and 2.2 kg of *Lumbricus* respectively, and the temperature of sesame oil was kept at 160° C. and stirred for 40 min to afford pharmaceutical composition 4.

Example 5

The pharmaceutical composition was prepared according to the method of example 1 except that the composition was consist of 10 Kg of beeswax and 90 Kg of sesame oil extract containing 2 kg of *Radix Scutellariae, Coptis Chinensis, Cortex Phellodendri, Pericarpium Papaveris* and *Lumbricus* respectively, and the temperature of sesame oil was kept at 155° C. and stirred for 40 min to afford pharmaceutical composition 5.

Example 6

The pharmaceutical composition was prepared according to the method of example 1 except that the composition was consist of 12 Kg of beeswax and 88 Kg of sesame oil extract containing 1 kg of *Radix Scutellariae, Coptis Chinensis, Cortex Phellodendri, Pericarpium Papaveris* and *Lumbricus* respectively, and the temperature of sesame oil was kept at 160° C. and stirred for 40 min to afford pharmaceutical composition 6.

Example 7

The pharmaceutical composition was prepared according to the method of example 1 except that the composition was consist of 4 Kg of beeswax and 96 Kg of sesame oil extract containing 7 kg of *Radix Scutellariae, Coptis Chinensis, Cortex Phellodendri, Pericarpium Papaveris* and *Lumbricus* respectively, and the temperature of sesame oil was kept at 155° C. and stirred for 40 min to afford pharmaceutical composition 7.

Example 8

Make the pharmaceutical composition in the present invention according to the method. The pharmaceutical composition was prepared according to the method of example 1 except that the composition was consist of 12 Kg of beeswax and 88 Kg of sesame oil extract containing 0.5 kg of *Radix Scutellariae, Coptis Chinensis, Cortex Phellodendri, Pericarpium Papaveris* and *Lumbricus* respectively, and the temperature of sesame oil was kept at 155° C. and stirred for 40 min to afford pharmaceutical composition 8.

Experimental Example 1

Figure 2:
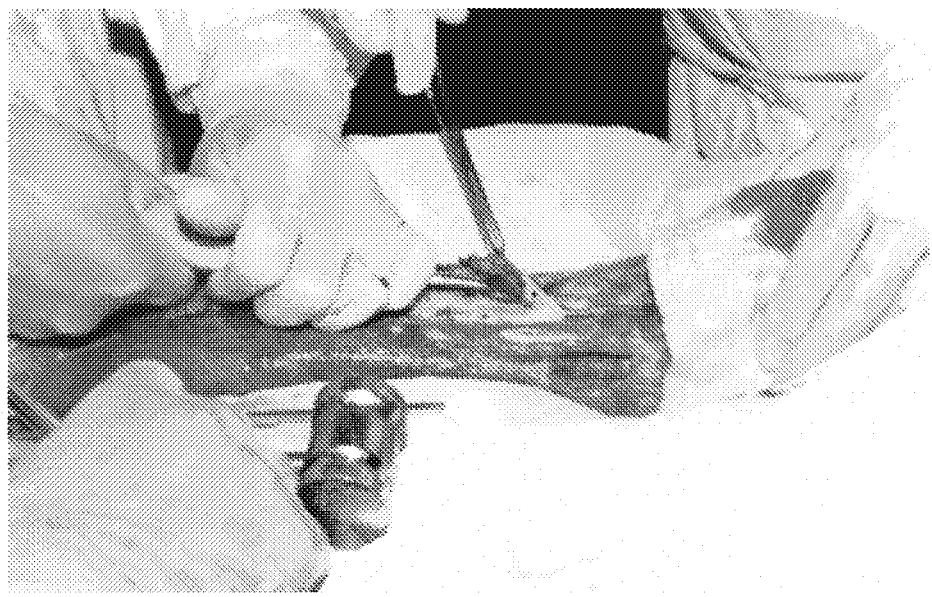
FIG. 2 is the photo of the application of the present pharmaceutical composition obtained in example 1 on the wounds directly and the removal of necrotic periosteum and tissues 2 days after the application in experimental example 1.

Referring to FIG. 1, Deep degree III burns combined with bone burn injury were firstly treated with pharmaceutical composition 7 and 8. In pharmaceutical composition 7 and 8, the individual weight proportion of *Radix Scutellariae, Coptis Chinensis, Cortex Phellodendri, Pericarpium Papaveris*, and *Lumbricus* is 0.5% and 7% respectively of the total weight of the sesame oil extract. The necrotic tissues of deep burns were liquefied and removed and the new granulation tissues grew out, while the burnt bone tissues still did not have vitality. Using the pharmaceutical composition 1 on the wounds directly and the necrotic tissues on the bone membrane and bone were removed after 2 days (FIG. 2).

Figure 3:
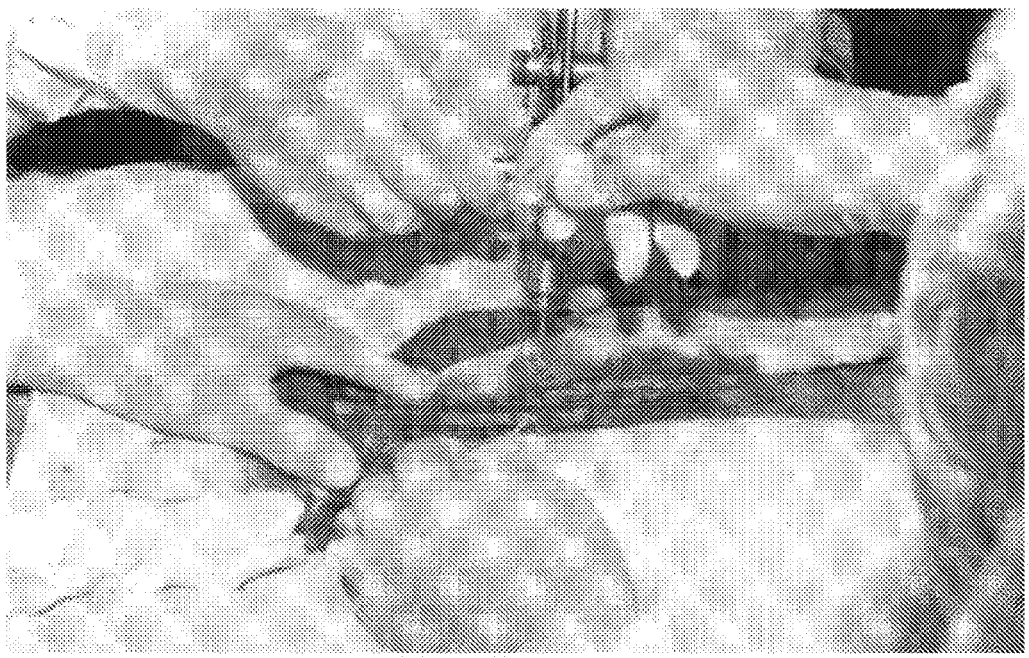
FIG. 3 is the photo of drilling the holes in the bone in experimental example 1.

Then drill the holes on the bone with 0.5 cm interval space and deep to the bone marrow until the seepage of bone marrow blood and then the pharmaceutical composition 1 was used directly to cover the drilled bones and holes with the thickness of about 1-3 mm. The dressing was changed twice in every morning and night respectively (FIG. 3).

Figure 4:
FIG. 4 is the photo of new skin regenerated from the original granulation wound and the new granulation tissues grew out from the drilled holes in experimental example 1.
Figure 5:
FIG. 5 is the photo of the new skin regenerated from the original granulation wound and the new granulation tissues grew out from the drilled holes in experimental example 1.
Figure 6:
FIG. 6 is the photo of the new skin regenerated from the bone granulation tissues in experimental example 1.
Figure 7:
FIG. 7 is the photo of the electrical injury of head top combined with osteocranium injury in experimental example 2.

After several days, the new skin regenerated from the original bone granulation tissues and the new granulation tissue grew out from the drilled holes (FIG. 4 and FIG. 5). After continuous application, the skin on the granulation tissues expanded and healed the wounds and the new granulation tissues grew out of the holes connected with each other and regenerated new skin on the new bone granulation tissues (FIG. 6).

Experimental Example 2

Referring to FIG. 2, the patient was subjected to the electrical injury on the top of head combined with skull periosteum burnt and skull surface necrosis. Firstly, the pharmaceutical composition 7 and 8 were used as the control drugs for 25 days. After treatment, there was no obvious improvement of skull necrotic surface. Then the pharmaceutical composition 2 obtained from example 2 was used to continue the treatment. The treatment method was to apply the pharmaceutical composition on the wounds directly with thickness of about 1-3 mm and the dressing was changed twice in every morning and night respectively for 7 days.

Figure 8:
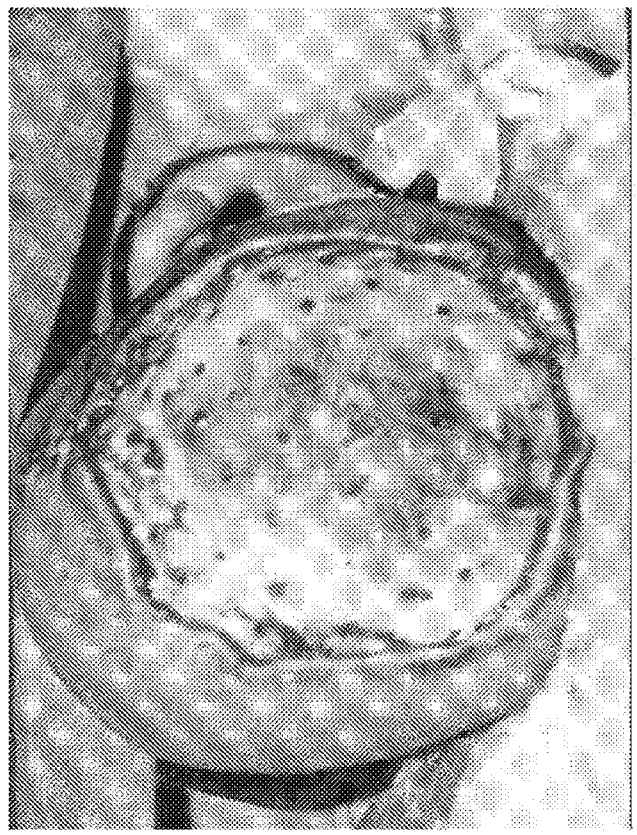
FIG. 8 is the photo of the drilled holes in skull bone after the surgical debridement of the necrotic tissues in experimental example 2.

After 7 days treatment, remove the necrotic bone tissues from outside to inside with surgical debridement and then drill the holes on the bones with drilling interval less than 1 cm until the bleeding of bone marrow. Then the pharmaceutical composition 2 was applied on the wounds with the thickness of about 1-3 mm and the dressing was changed twice in every morning and night respectively (FIG. 8).

Figure 9:
FIG. 9 is the photo showing the wound condition after 10 days treatment in experimental example 2.

After 10 days, the granulation tissues grew out of the drilled holes and new skin gradually regenerated and connected with each other to close the bone wounds (FIG. 9).

Figure 10:
FIG. 10 is the photo showing the healing of the damaged tissues in experimental example 2.
Figure 11:
FIG. 11 shows the electron microscope photo of the slices of healed skin in experimental example 2.
Figure 12:
FIG. 12 shows the electron microscope photo of the slices of healed skin in experimental example 2.

After the bone wounds healed, the skin tissues can be seen (FIG. 10). The electron microscope slices shows the structures of epidermis, dermis and appendixes (except the hair follicles) (FIG. 11 and FIG. 12).

In addition, the pharmaceutical composition 1, 3-6 also have the same therapeutic effect in the patient (data omitted).

Experimental Example 3

Figure 13:
FIG. 13 shows the open fracture wounds in experimental example 3.

The open fracture wound is often contaminated by the laceration, the wound infection and soft tissue non-healing is a difficult medical problem and the severe patient may facing amputation. This difficult medical problem was solved effectively by the application of the present pharmaceutical composition combined with the current surgical debridement and orthopedic operation. During the Wenchuan Earthquake in 2008, the present pharmaceutical composition was used to treat the patients with open fracture wounds and achieved surprising effects in that the wound healed fast, infection was reduced, and the fracture bone grew fast, effectively avoiding the amputation (FIG. 13).

Figure 14:
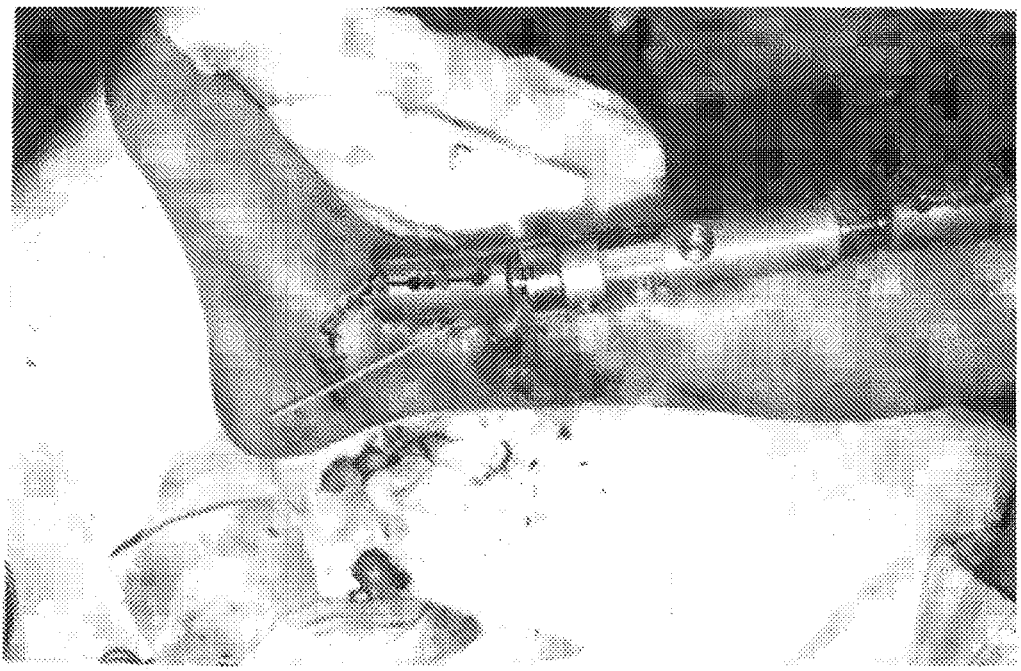
FIG. 14 shows the conditions after the fracture fixation and wounds suture in experimental example 3.

After the accident of open fracture, the present pharmaceutical composition 3 was applied on the wounds directly as early as possible. It can not only protect the wounds, isolate the wounds from the air and avoid the contamination, but also play the function of metabolizing the contaminants and debriding the wounds without further damage. The mechanical fixation operation on the fractured bone tissue can be done after cleaning the wounds with normal saline. After the surgical suture of soft tissue and skin, the pharmaceutical composition 3 was applied again on the sutured wounds, which can prevent the infection and promote the wound healing. FIG. 14 shows the wound conditions after the bone fixation and suture.

Figure 15:
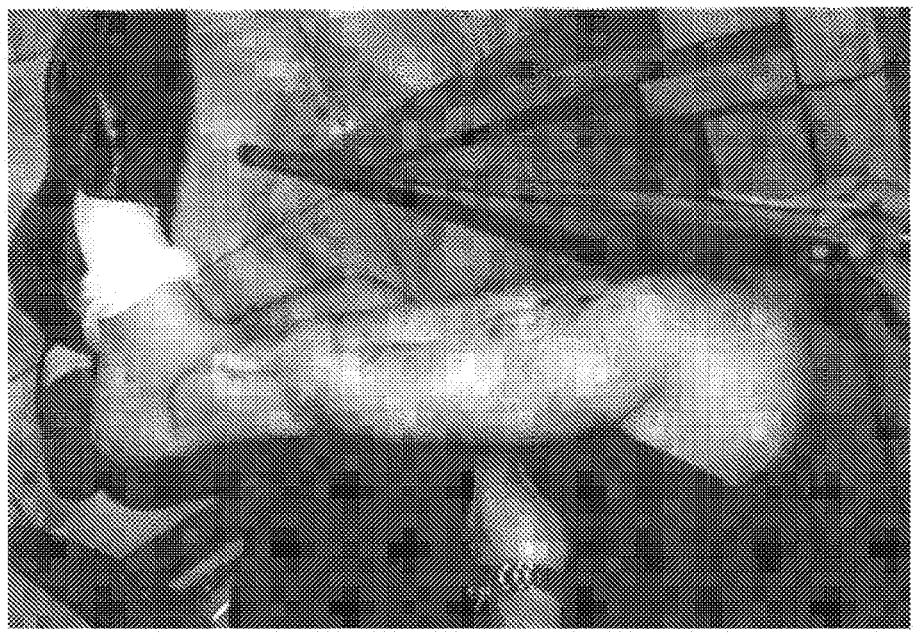
FIG. 15 shows the healed open fracture in experimental example 3.
Figure 16:
FIG. 16 shows the defect injury of severe skull bone electrical injury in experimental example 4.
Figure 17:
FIG. 17 shows the defect injury of severe skull bone electrical injury in experimental example 4.

After 40 days treatment, there was no infection on the wounds, the defected skin tissue and other soft tissues were healed (FIG. 15).

In addition, the present pharmaceutical composition 4 and 5 also achieved the same therapeutic effect on the patients.

The inventor found that for a pharmaceutical composition with the contents of such raw materials as *Radix Scutellariae, Coptis Chinensis, Cortex Phellodendri, Pericarpium Papaveris* and *Lumbricus* being higher than 6% or lower than 1% by dry weight of the total weight of the sesame oil extract, it has no ideal therapeutic effect on open fracture, especially on the bone recovery. It is speculated that the higher content (higher than 6%) of *Radix Scutellariae, Coptis Chinensis, Cortex Phellodendri, Pericarpium Papaveris* and *Lumbricus* in sesame oil extract may inhibit the cell growth on wounds; and the lower content (lower than 1%) of *Radix Scutellariae, Coptis Chinensis, Cortex Phellodendri, Pericarpium Papaveris* and *Lumbricus* in sesame oil extract does not reach the therapeutic dosage, which cannot promote the cell growth on the wounds.

Example 4

The severe skull electronic burn injury is also a medical problem currently, as there is lack of nutrition sources for the bone tissues, bone tissues are partially defected, and it is difficult to repair the bone tissues by the nutrition supply through bone marrow tissues. The pharmaceutical composition 4 was used directly as the culture media of bone tissues, soft tissues, and skin of the severe electrical burn injury patient combined with skull bone injury, which can directly repair the severe damaged bone tissues and heal the wounds.

Figure 18:
FIG. 18 shows the wounds after the application of the present pharmaceutical composition 4 in experimental example 4.
Figure 19:
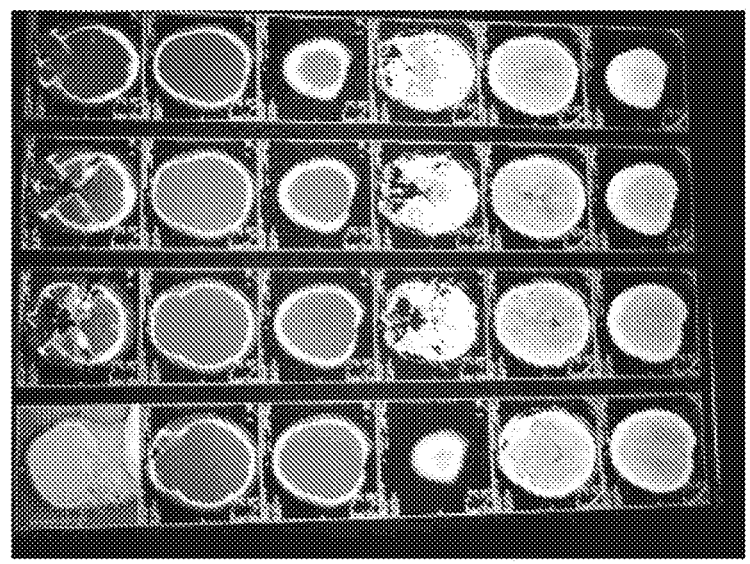
FIG. 19 shows the X-ray image of skull bone in experimental example 4.

Firstly, under the protection of the pharmaceutical composition 4, parts of the skull bone necrotic tissues were removed with the surgical debridement (FIG. 18) and X-ray examination shows that most of the bone tissues at the top of skull were defected and the depth of wounds reached to the endomeninx, which indicates that parts of the bone marrow tissues are defected (FIG. 19).

The pharmaceutical composition 7 and 8 were used as the control drugs for 25 days, there was no obvious improvement at the necrotic skull bone surface.

Then the bone tissues with partial defect were drilled and the pharmaceutical composition 4 and control drugs were continued to be used to incubate the granulation tissues. The present pharmaceutical composition 4 and control drugs were applied to cover the wounds directly with the thickness of about 1-3 mm and the dressing was changed twice in every morning and night respectively.

The skull bone of patients has no improvement after using the control drugs and then the pharmaceutical composition 4 was used to continue treatment.

Figure 20:
FIG. 20 shows the growing conditions of skull skin in experimental example 4.
Figure 21:
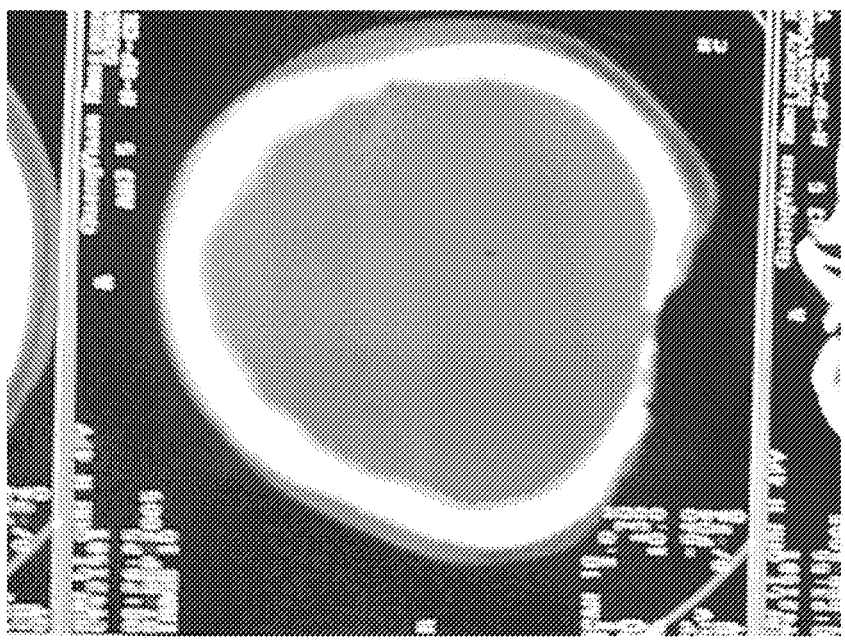
FIG. 21 shows the X-ray image in experimental example 4.

The wound conditions after using the pharmaceutical composition 4 to incubate the bone tissues and soft tissues in situ were that the surrounding soft tissues were regenerated and the bone tissues surrounded and in the central were growing under the effect of drug (FIG. 20). X-ray image shows that the skull bone in the middle of meninx area was growing under the protection (FIG. 21).

Figure 22:
FIG. 22 shows obvious regeneration of bone tissues and the significantly decreased exposed area of periosteum 40 days after the treatment in experimental example 4.

After 40 days treatment, there was obvious growth of bone tissues and the exposed area of bone membrane became smaller (FIG. 22).

Figure 23:
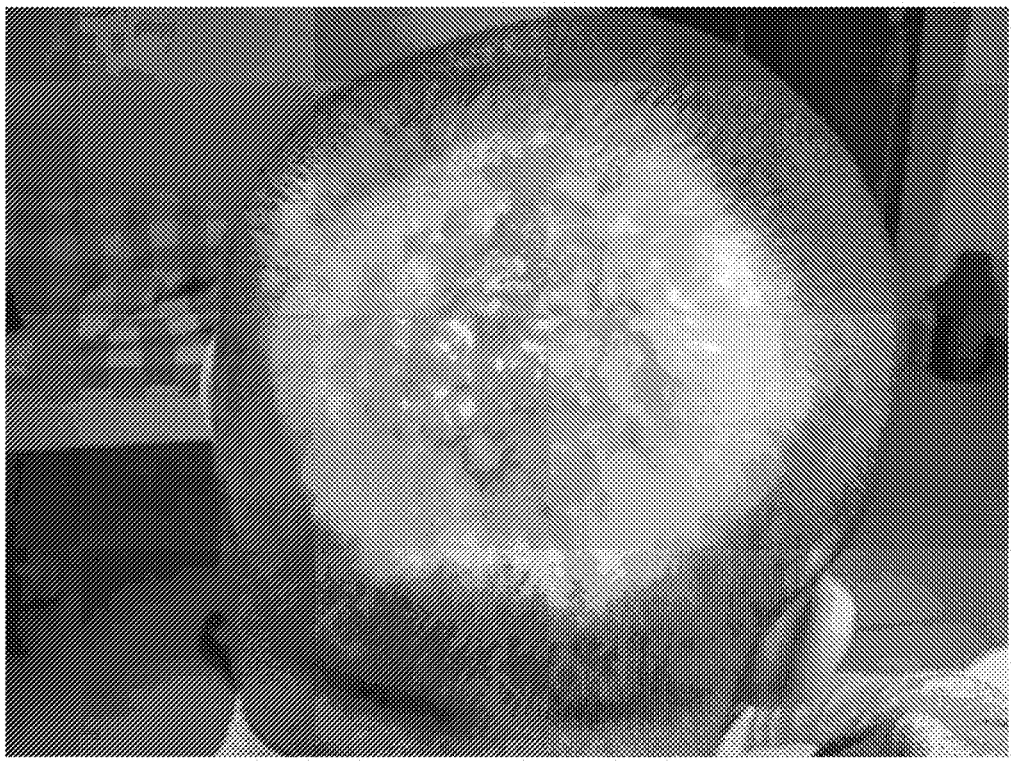
FIG. 23 shows the restoration of skull bone, soft tissues, and skin in experimental example 4.

The treatment was continued until the regenerative restoration in situ of skull bone was realized: the exposed area of bone membrane became smaller and smaller, the regenerative restoration of soft tissues and skin were realized and finally the wound healed (FIG. 23).

Figure 24:
FIG. 24 shows the growing of head hair after the healing of skull wounds and plastic surgery of head skin in experimental example 4.

The head skin plastic surgical operation was performed after the healing of the skull bone and wounds, and the hair of the patients can cover most of the head (FIG. 24).

Same excellent treatment effects can be achieved with the pharmaceutical composition 5 and 6 in the similar tests to the above one.

Experimental Example 5

Figure 25:
FIG. 25 shows the severe burn injury of neck, head, and face in experimental example 5.

Male, 29 years old patient was suffering from the severe neck, head, and facial burn injury after carbon monoxide poisoning (FIG. 25). The bone surface of the patient was severe necrotic and there was no granulation tissue growth after regional treatment of surgery and there was no vitality of bone tissue.

Figure 26:
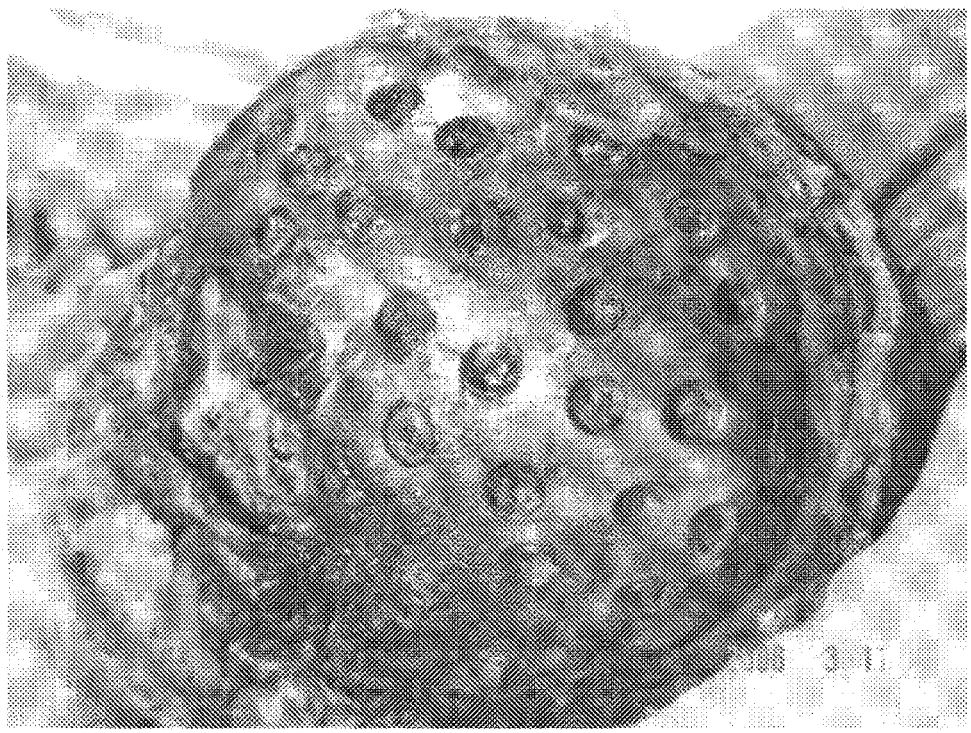
FIG. 26 shows the wound condition after the application of the control drug C of experimental example 4 in example 5.

The skull bone of the patient was drilled holes and then iodine treatment was continued for 9 days followed by the application of the pharmaceutical composition 7 and 8 as control drugs for another 10 days, but there was no granulation tissue growth and viable bone tissue (FIG. 26).

Figure 27:
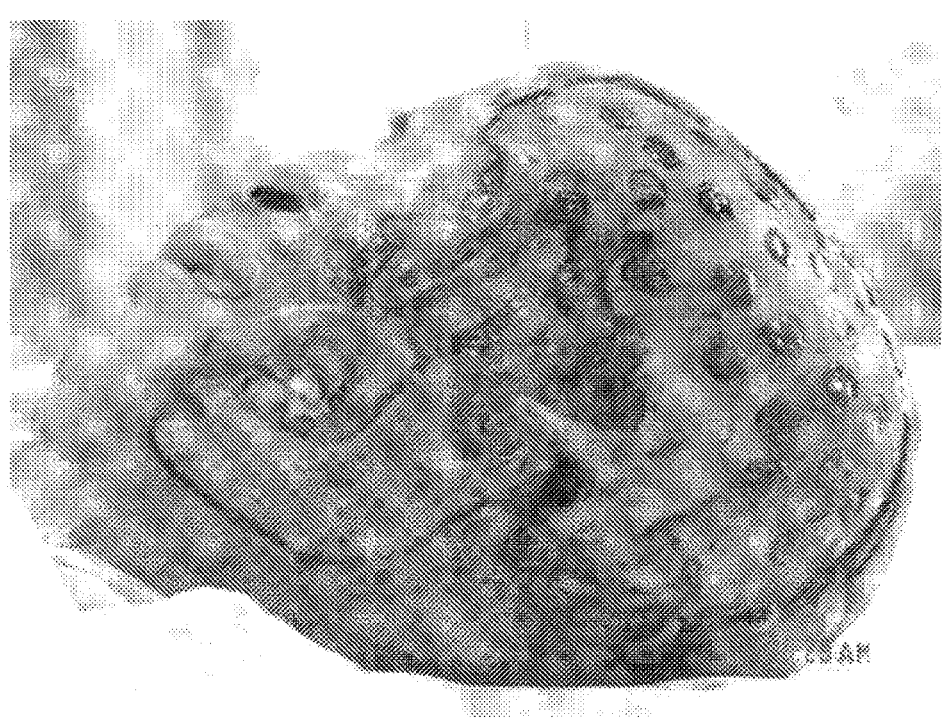
FIG. 27 shows the wound conditions after the application of the pharmaceutical composition 5 in example 5.
Figure 28:
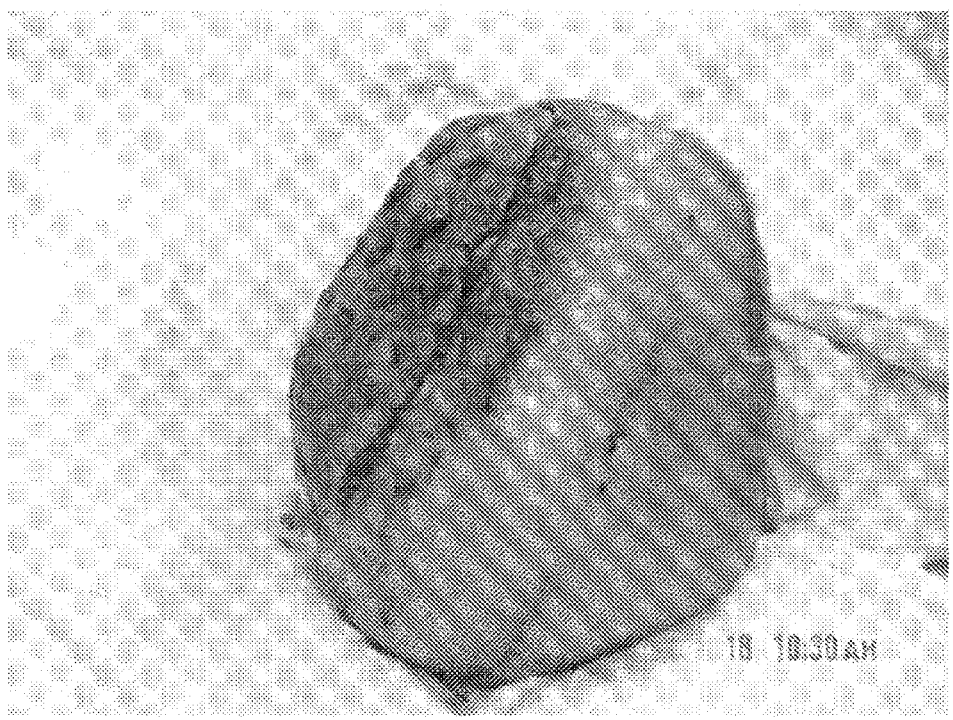
FIG. 28 shows the wound conditions after the application of the pharmaceutical composition 5 in example 5.

Then, the pharmaceutical composition 5 was used immediately with thickness of 3 mm on the wounds to cover the wounds completely. After 5 days treatment, the necrotic-like bone tissues recovered vitality and the granulation tissues grew out of the drilled holes and the vitality of bone surface recovered and gradually formed periosteum. At this time, the wound was almost ready for skin flap grafting. The granulation tissues were incubated and maintained continuously in the vital environment of bone surface until a proper time was selected for skin flap grafting to cover the entire exposed bones (FIG. 27 and FIG. 28).

Figure 29:
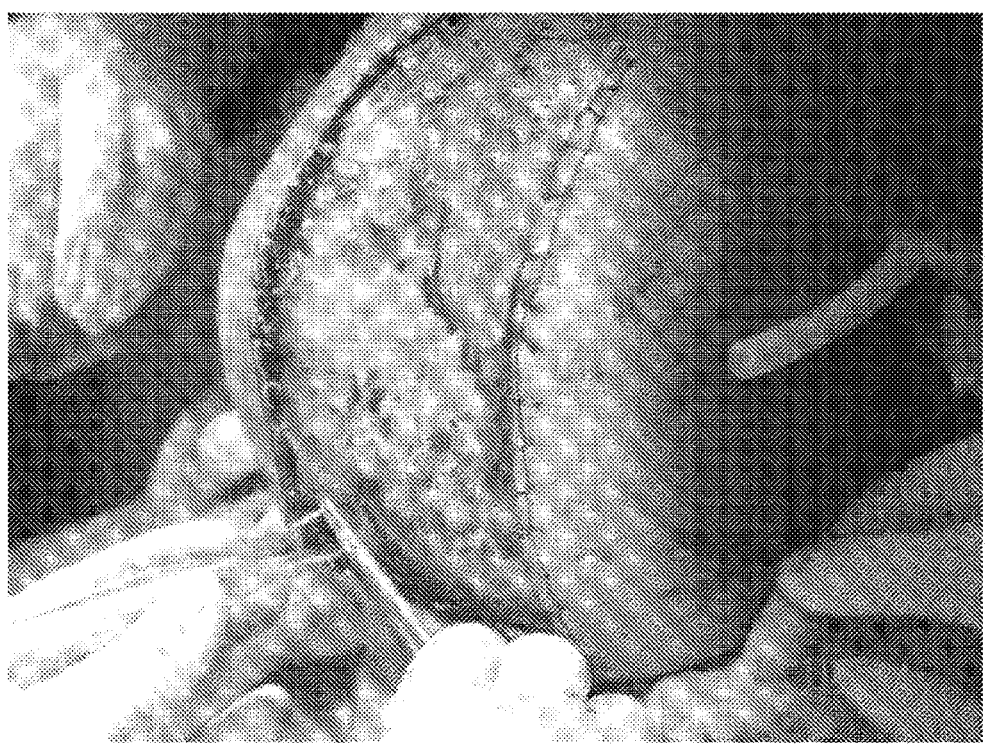
FIG. 29 shows the skin flap grafting in example 5.
Figure 30:
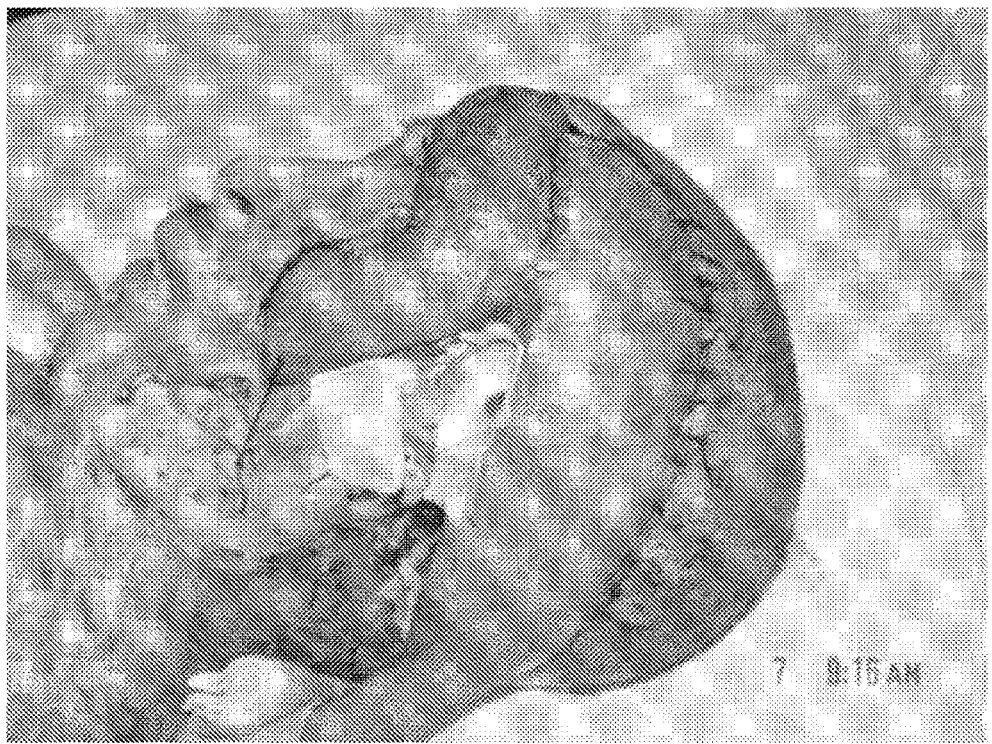
FIG. 30 shows the skin flap grafting in example 5.
Figure 31:
FIG. 31 shows the skin flap grafting in example 5.

The free skin flaps from the patient's back (FIG. 29 and FIG. 30) was taken for the head skin flap grafting, and the wound of the patient recovered gradually (FIG. 30).

What is claimed is:

1. A method of treating open traumas of a fracture and/or deep thermal injury with bone injury and/or osteonecrosis in a warm-blooded animal in need thereof comprising administering a composition comprising:
    4%-12% of beeswax by weight based on the total weight of said composition, and
    88%-96% of sesame oil extract by weight based on the total weight of said composition,
    wherein the sesame oil extract contains therapeutically effective amounts of *Radix Scutellariae, Coptis Chinensis, Cortex Phellodendri, Pericarpium Papaveris*, and *Lumbricus*,
    to said warm-blooded animal in need thereof to effectively treat the open traumas of a fracture and/or deep thermal injury with bone injury and/or osteonecrosis in the warm-blooded animal in need thereof.

2. The method of claim 1, wherein each of the *Radix Scutellariae, Coptis Chinensis, Cortex Phellodendri, Pericarpium Papaveris*, and *Lumbricus* based on their dry weight is 2%-4% of the total weight of the sesame oil.

3. The method of claim 1, wherein each of the *Radix Scutellariae, Coptis Chinensis, Cortex Phellodendri, Peri-* carpium Papaveris, and Lumbricus based on their dry weight is 3% of the total weight of the sesame oil.

4. The method of claim 1, wherein the composition comprises:
   4% of beeswax by weight based on the total weight of said composition; and
   96% of sesame oil extract by weight based on the total weight of said composition,
   wherein the sesame oil extract contains 6% Radix Scutellariae, 6% Coptis Chinensis, 6% Cortex Phellodendri, 6% Pericarpium Papaveris, and 6% Lumbricus, each component by dry weight based on the total weight of the sesame oil.

5. The method of claim 1, wherein the composition comprises:
   6% of beeswax by weight based on the total weight of said composition; and
   94% of sesame oil extract by weight based on the total weight of said composition,
   wherein the sesame oil extract contains 3% Radix Scutellariae, 3% Coptis Chinensis, 3% Cortex Phellodendri, 3% Pericarpium Papaveris, and 3% Lumbricus, each component by dry weight based on the total weight of the sesame oil.

6. The method of claim 1, wherein the composition comprises:
   8% of beeswax by weight based on the total weight of said composition; and
   92% of sesame oil extract by weight based on the total weight of said composition,
   wherein the sesame oil extract contains 1% Radix Scutellariae, 1% Coptis Chinensis, 1% Cortex Phellodendri, 1% Pericarpium Papaveris, and 1% Lumbricus, each component by dry weight based on the total weight of the sesame oil.

7. The method of claim 1, wherein the composition comprises:
   8% of beeswax by weight based on the total weight of said composition; and
   92% of sesame oil extract by weight based on the total weight of said composition,
   wherein the sesame oil extract contains 5.5% Radix Scutellariae, 5.5% Coptis Chinensis, 5.5% Cortex Phellodendri, 2.2% Pericarpium Papaveris, and 2.2% Lumbricus, each component by dry weight based on the total weight of the sesame oil.

8. The method of claim 1, wherein the composition comprises:
   10% of beeswax by weight based on the total weight of said composition; and
   90% of sesame oil extract by weight based on the total weight of said composition,
   wherein the sesame oil extract contains 2% Radix Scutellariae, 2% Coptis Chinensis, 2% Cortex Phellodendri, 2% Pericarpium Papaveris, and 2% Lumbricus, each component by dry weight based on the total weight of the sesame oil.

9. The method of claim 1, wherein the composition comprises:
   12% of beeswax by weight based on the total weight of said composition; and
   88% of sesame oil extract by weight based on the total weight of said composition,
   wherein the sesame oil extract contains 1% Radix Scutellariae, 1% Coptis Chinensis, 1% Cortex Phellodendri, 1% Pericarpium Papaveris, and 1% Lumbricus, each component by dry weight based on the total weight of the sesame oil.

10. The method of claim 1, wherein said bone injury comprises bone injury with periosteum damage.

11. The method of claim 1, wherein said administration comprises applying the composition onto the affected locations with a thickness of about 1-3 mm.

12. The method of claim 11, wherein said administration comprises applying the composition onto the affected locations with a thickness of 3 mm.

13. The method of claim 1, wherein the composition is administered as a multiple dose treatment.

14. The method of claim 13, wherein the multiple dose treatment occurs over a time period of from 7 to 40 days.

15. The method of claim 14, wherein the multiple dose treatment occurs over a time period of 7 days.

16. The method of claim 14, wherein the multiple dose treatment occurs over a time period of 10 days.

17. The method of claim 14, wherein the multiple dose treatment occurs over a time period of 40 days.

18. The method of claim 1, wherein each of the Radix Scutellariae, Coptis Chinensis, Cortex Phellodendri, Pericarpium Papaveris, and Lumbricus based on their dry weight is 1%-6% of the total weight of the sesame oil.

19. The method of claim 1, wherein the open traumas complicated by fracture and/or deep thermal injury with bone injury and/or osteonecrosis are on a human being.

20. The method of claim 1, wherein the bone injury is selected from shin bone injury, skull bone injury, and/or cartilage injury.

* * * * *